United States Patent [19]

Lobazov et al.

[11] Patent Number: 4,822,167
[45] Date of Patent: Apr. 18, 1989

[54] LASER FLUOROMETRIC DETECTOR FOR MICROCOLUMN CHROMATOGRAPHY

[75] Inventors: Alexandr F. Lobazov; Vasily A. Mostovnikov; Sergei V. Nechaev, all of Minsk; Boris G. Belenky, Leningrad, all of U.S.S.R.

[73] Assignee: Institute Fiziki AN BSSR, Minsk, U.S.S.R.

[21] Appl. No.: 903,650

[22] Filed: Sep. 5, 1986

[51] Int. Cl.[4] .............................................. G01J 3/30
[52] U.S. Cl. ..................................... 356/317; 356/318
[58] Field of Search ................................ 356/317, 318

[56] References Cited

U.S. PATENT DOCUMENTS

| | | | |
|---|---|---|---|
| 4,031,399 | 6/1977 | Klein et al. | 356/317 |
| 4,191,475 | 3/1980 | Sourroville | 356/318 |
| 4,203,670 | 5/1980 | Bromberg | 356/318 X |
| 4,350,892 | 9/1982 | Kay et al. | 356/318 X |
| 4,461,573 | 7/1984 | Lucht et al. | 356/318 |
| 4,537,861 | 8/1985 | Elings et al. | 356/317 X |
| 4,548,499 | 10/1985 | Eisert et al. | 356/318 |
| 4,555,177 | 11/1985 | Barrett | 356/318 |
| 4,643,566 | 2/1987 | Ohe et al. | 356/317 X |

OTHER PUBLICATIONS

H. Todoriki, A. Hirakawa, "Chemical & Pharmaceutical Bulletin", vol. 28, No. 4, 1980, pp. 1337-1339.
L. W. Hershberger, J. B. Callis, and G. D. Christian, "Analytical Chemistry", vol. 51, No. 9, Aug. 1979, pp. 1444-1446.

Primary Examiner—Thomas H. Tarcza
Assistant Examiner—Mark Hellner
Attorney, Agent, or Firm—Lilling & Greenspan

[57] ABSTRACT

A laser fluorometric detector for microcolumn chromatography includes the following optically connected components: a laser, a cylindrical telescope, an adjustable diaphragm which has the shape of a rectangular trapezium, a flow-through cell which is a parallelepiped with a through-going square channel, and a fluoroescence emission receiver.

1 Claim, 1 Drawing Sheet

LASER FLUOROMETRIC DETECTOR FOR MICROCOLUMN CHROMATOGRAPHY

BACKGROUND OF THE INVENTION

1. Field of the Invention

The invention relates to laser spectroscopy and, in particular, relates to laser fluorometric detectors for microcolumn chromatography, and can be used for detecting ultratrace amounts of fluorescent liquids.

2. Description of the Prior Art

The following requirements are usually the goals in the development of LC detectors: high sensitivity, low detection limit, low noise level, and broad linearity range. In addition, chromatographic peak resolution also imposes certain limitations on the design of the cell. It should have a limited volume, the isolated components should not mix, and the detector channel should be capable of being washed very fast.

The concentrational sensitivity of the detector is proportional to the amount of the substance in the measuring cell. To leave the detector resolution unaffected, the following condition should be observed:

$$V_o \leq \tfrac{1}{2} V_1 = Sl/\sqrt{M}, \qquad (1)$$

where $V_o$ is the detected volume including the cell volume and the volume of the detector channel from the outlet of the chromatographic column to the measuring cell;

$V_1$ is the volume of the effluent in a chromatographic peak;

S is the ID area of the column; and l is the column length.

On the other hand, if $V_o << V_1$, the detector sensitivity drops, since the amount of the substance in the cell becomes less. Each chromatographic column has, therefore, its own optimal volume of detection, which should be selected.

Known in the art is a laser fluorometric detector for microcolumn chromatography (cf., for example, L.W. Hershberger, J.B. Callis, and G.D. Christian, Analytical Chemistry, Vol. 51, No. 9, August 1979, pp. 1444-1446), which comprises several optically connected components: a laser, a unit for forming laser emission, a flow-through cell designed for communication with the chromatographic column, and a receiver of fluorescence emission.

The flow-through cell of this detector is a chamber with quartz windows on each of the four sides. The internal volume of the chamber is filled with the effluent which is also used in the flow channel of the chromatographic column. The lower part of the chamber is fitted with a hydrodynamic jet nozzle through which the sample is injected. The fluorescence emission is collected by the objective of the receiver in a direction perpendicular to the excitation radiation.

The disadvantage of this detector is its insufficient sensitivity.

This is due to the fact that the detected volume of the effluent is substantially smaller in relation to the volume of the chromatographic peaks, since the cross-section of the stream flowing through the cell is substantially less than the cross-section of the internal diameter of the chromatographic column. One more contributing factor consists in that the sample stream is surrounded by the effluent stream whose thickness exceeds the sample stream diameter by a factor of 10 to 20. Fluorescence of the effluent, which adds to the noise level, is a serious handicap to the useful signal recording.

Also known in the art is a laser fluorometric detector for microcolumn chromatography (cf., for example, H.Todoriki, A.Hirakawa, Chemical & Pharmaceutical Bulletin, Vol. 28, No. 4, 1980, pp. 1337-1339), comprising the following optically connected components: a laser, a laser emission forming unit, a flow-through cell intended for communication with the chromatographic column, a diaphragm for adjusting the sample volume in the cell, and a fluorescence emission receiver.

The flow-through cell in this device is a quartz tube with another quartz tube, of a lesser diameter, connected perpendicular thereto as a sample inlet. An optical fiber is introduced into the upper end of the flow cell, a micro-lens being attached to the exit end of the fiber, which is the laser emission forming unit.

The micro-lens is placed somewhat above the region where the two tubes are connected in order to reduce the divergence of the laser beam after the fiber. The fluorescence signal is produced in the zone where the flowing sample enters the large-diameter tube from the smaller-diameter tube. The fiber with the micro-lens is placed so that the diverging laser beam does not reach the tube walls in the zone where the fluorescence emission is collected. This zone can be selected by means of a round adjustable diaphragm installed on one axis with the sample inlet tube. In this manner the photoreceiver is protected from the scattered laser light.

This device is deficient in that the resolution of the detector is not high enough. Chromatographic fractions are seriously disturbed when the sample flow turns from the smaller diameter tube into the larger diameter tube, and the laminar nature of the stream is upset.

In addition, in the two above detectors fluorescence was excited by an unparallel laser beam, since the latter is focused by spherical lenses. This, in turn, adds to the scattered laser radiation on the boundaries where media having different refractive indices meet.

Also, the above detectors do not provide for optimal selection of sample volumes for different microcolumns. In case the microcolumn is replaced by another, the sensitivity or resolution of detection can be affected.

SUMMARY OF THE INVENTION

It is an object of the invention to improve the sensitivity and resolution of the laser fluorometric detector for microcolumn chromatography.

There is provided a laser fluorometric detector for microcolumn chromatography, which comprises the following optically connected components: a laser, a unit for forming laser emission, a flow-through cell intended for communication with the chromatographic microcolumn, a diaphragm for adjusting the volume of the sample in the cell, and a receiver of fluorescence emission. A according to the invention, the laser emission forming unit is a cylindrical telescope. The flow-through cell is a right-angle parallellepiped having an internal through-going square channel, placed so that the longitudinal axis of the channel is perpendicular to the direction of the collimated laser light. The diaphragm for adjusting the detected sample volume is a rectangular trapezium located between the cylindrical telescope and the flow-through cell so that the bases of said trapezium are parallel to the channel axis, and is provided with a means for travelling in the plane thereof and in the direction perpendicular to the trapezium bases.

The laser fluorometric detector for microcolumn chromatography, according to the invention, offers the advantages of smooth adjustment of the detected sample volume in accordance with the parameters of the particular chromatographic microcolumn being used. The sensitivity and resolution of the detector are high due to the optimal selection of the detected sample volume. The flow-through cell and collimated laser radiation obtained at the outlet of the cylindrical telescope bring the effect of the scattered laser light on the receiver of fluorescence emission to a minimum. The flow-through cell is designed so that the sample flow in the zone where fluorescence emission is collected remains laminar.

BRIEF DESCRIPTION OF THE DRAWINGS

The invention will now be described in greater detail, by way of example, with reference to the accompanying drawings, wherein.

DESCRIPTION OF THE INVENTION

Figure 1:
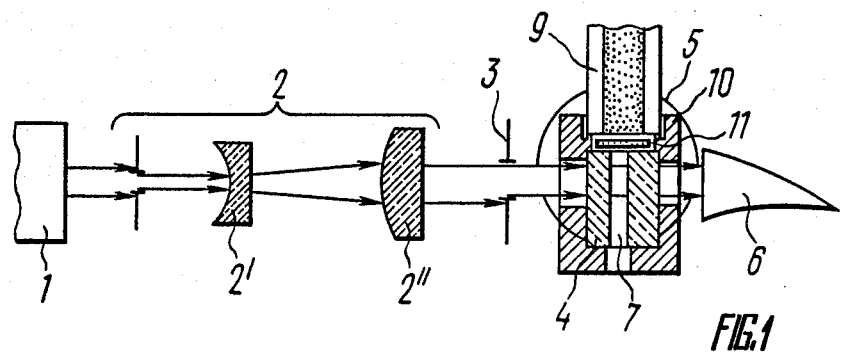
FIG. 1 shows an optical arrangement of a laser fluorometric detector for microcolumn chromatography with a chromatographic microcolumn, according to the invention.
Figure 2:
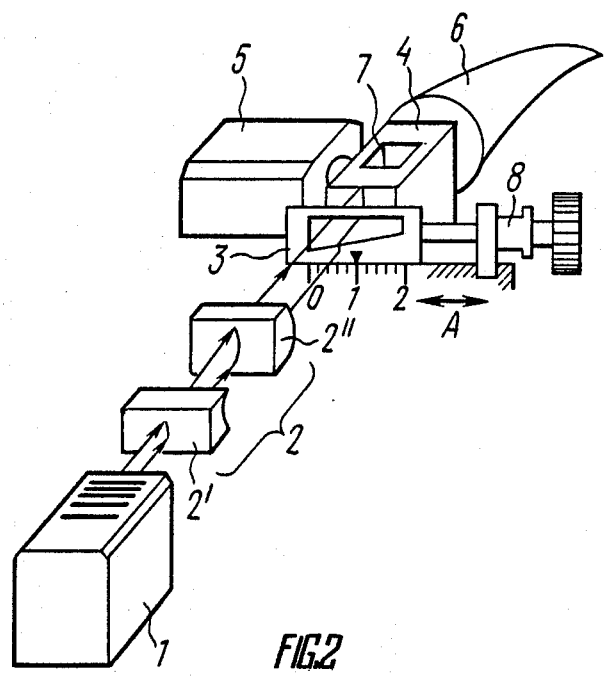
FIG. 2 shows the arrangement of FIG. 1 and an isometric view of the detector without the microcolumn, according to the invention.

A laser fluorometric detector for microcolumn chromatography, which is shown in FIGS. 1 and 2, includes the following optically connected and successively arranged components: a laser 1, a unit for forming laser radiation, which is a cylindrical telescope 2, a diaphragm 3 for adjusting the detected sample volume, a flow-through cell 4 which is the measuring cell of the detector, a receiver 5 of fluorescence emission, and a light trap 6. The receiver 5 is placed so that the optical axis of the inlet objective thereof is perpendicular to the axis of the laser beam. The cylindrical telescope 2 is composed of two lenses 2' and 2", the negative lens 2' and the positive lens 2". The flow-through cell 4 is a rectangular parallelepiped with a through-going internal channel 7 which has a square cross-section. The flow-through cell 4 is placed so that the longitudinal axis of the channel 7 is perpendicular to the direction of the collimated laser light. The diaphragm 3 for adjusting the detected sample volume is a rectangular trapezium which is placed between the cylindrical telescope 2 and the flow-through cell 4 so that the bases of the trapezium are parallel to the longitudinal axis of the channel 7. The diaphragm 3 is provided with a means 8 for travelling in the plane thereof and in the direction perpendicular to the bases of the trapezium, which is indicated by arrow A in FIG. 2. The means 8 can, for example, be a micrometer screw.

A chromatographic column 9 is secured by a threaded connection at the outlet butt end of the flow-through cell 4 which is confined in a metal holder 10. A teflon ring with a cermet filter 11 is placed between the flow-through cell 4 and the column 9.

the laser fluorometric detector, according to the invention, operates as follows.

The effluent of the chromatographic column 9, which consists of separated fractions of the substance to be analyzed, is fed through the cermet filter 11 to the through-going channel 7 of the flow-through cell 4, the laminar flow being left undisturbed. The laser beam is transformed by the cylindrical telescope 2 from a round beam into a flat one. The width of the cross-section of the flat beam is equal to that of the channel 7 where the sample flows. The length of the laser beam cross-section can be adjusted by means of the trapezium-shaped diaphragm 3 located in front of the flow-through cell 4 which is the measuring cell of the detector. The laser beam passes through the cell 4 and the column of the liquid being analyzed. Fluorescence is excited in this column of liquid and extinguished in the light trap 6. The fluorescence emission is collected by the objective of the receiver 5 which can be a photomultiplier in a plane perpendicular to the laser beam.

Scattering of the laser radiation is substantially diminished by the rectangular shape of the flow-through cell 4 made of non-luminescent quartz, and the square shape of the internal through-going channel 7.

The adjustable diaphragm 3 which is a rectangular trapezium is placed so that its side perpendicular to the bases is also parallel to the wall of the flow-through cell 4 and is located on a level with the butt end of this cell 4, to which the chromatographic microcolumn 9 is attached. This position of the diaphragm 3 offers the advantage of exciting fluorescence in the sample immediately after it leaves the column 9. The effluent volume, therefore, can be brought to a minimum. Moreover, the diaphragm 3 can be moved in the direction of the arrow A and in this manner the height of the column of the liquid excited by laser light can be smoothly adjusted, while the power density remains unchanged. This permits selection of an optimal sample detection volume for each particular chromatographic column, which contributes to the sensitivity and resolution of the analysis.

A prototype of the laser fluorometric detector for microcolumn chromatography has been manufactured according to the invention.

The measuring cell 4 of the square-shaped detector was made of quartz which produces no luminescence when subjected to laser radiation. The measuring cell dimensions were $4 \times 10 \times 20$ mm, the internal channel was $0.5 \times 0.5$ mm. The cylindrical telescope produced a laser beam whose cross-section was a stripe measuring $0.5 \times 7$ mm. The diaphragm 3 restricted the stripe to a length of from 1 to 6 mm in order to produce a strictly rectangular cross-section of the laser beam wherein the power is uniformly distributed. The detected sample volume could be smoothly adjusted from 0.25 to 1.5 microliters. In all cases the after-column volume of the detector did not exceed 0.05 microleters. Fluorescence emission was excited at the wavelength of 325 nm and recorded at 550 nm. Using a $0.6 \times 170$ mm microcolumn ($M = 8 \cdot 10^3$), the threshold sensitivity of the detector was $2 \cdot 10^{-16}$ moles in the chromatographic peak of disodium salts of aminoacids.

What is claimed is:

1. A laser fluorometric detector for microcolumn chromatography, comprising:
    a laser producing a laser beam having a round cross-section;
    a unit for shaping laser emission, placed in the path of said laser beam, which comprises a cylindrical telescope, said cylindrical telescope transforming said laser beam having a round cross-section into a substantially flat beam defining a first plane;

a diaphragm defining a second plane for adjusting the detected sample volume, having the shape of a rectangular trapezium, located in the path of said flat laser beam so that the bases of said trapezium are parallel to said first plane into which said laser beam is flattened, said diaphragm being adapted to travel in said second plane and in a direction perpendicular to said first plane;

a flow-through cell being shaped as a rectangular parallelepiped, having a lateral face which is an inlet face for said laser beam, an outlet face located opposite said inlet face, and two butt faces;

a through-going channel in said cell, having a square cross-section, the longitudinal axis of said channel being parallel to the edges of said flow-through cell, the inlet of said channel being located on one butt face and the outlet on the other butt face of said cell, said flow-through cell being placed so that the inlet face thereof is perpendicular to said plane of the laser beam, the longitudinal axis of said channel intersecting said laser beam, when the latter passes through said flow-through cell, said butt face of the flow-through cell, where the inlet of the channel is located, being adapted for communication with said chromatographic column for feeding the sample liquid into said through channel;

a laser radiation trap located opposite said outlet face of said flow-through cell; and a receiver of fluorescence emission, having an objective adapted to receive radiation from the lateral face of said cell, which is perpendicular to the said inlet and outlet faces.

* * * * *